United States Patent [19]
Klicek

[11] Patent Number: 5,496,312
[45] Date of Patent: Mar. 5, 1996

[54] IMPEDANCE AND TEMPERATURE GENERATOR CONTROL

[75] Inventor: Michael S. Klicek, Boulder, Colo.

[73] Assignee: Valleylab Inc., Boulder, Colo.

[21] Appl. No.: 133,235

[22] Filed: Oct. 7, 1993

[51] Int. Cl.$^6$ ................................................ A61B 17/36
[52] U.S. Cl. ........................ 606/34; 606/49; 606/50; 606/51
[58] Field of Search ................... 606/32–35, 37–52

[56] References Cited

U.S. PATENT DOCUMENTS

| | | |
|---|---|---|
| 2,827,056 | 3/1958 | Degelman . |
| 3,964,487 | 6/1976 | Judson . |
| 3,980,085 | 9/1976 | Ikuno . |
| 4,092,986 | 6/1978 | Schneiderman . |
| 4,094,320 | 6/1978 | Newton et al. . |
| 4,188,927 | 2/1980 | Harris . |
| 4,232,676 | 11/1980 | Herczog . |
| 4,314,559 | 2/1982 | Allen . |
| 4,321,926 | 3/1982 | Roge . |
| 4,372,315 | 2/1983 | Shapiro et al. . |
| 4,492,231 | 1/1985 | Auth . |
| 4,658,815 | 4/1987 | Farin et al. ................... 606/34 |
| 4,658,819 | 4/1987 | Harris et al. . |
| 4,860,745 | 8/1989 | Farin et al. . |
| 5,122,137 | 6/1992 | Lennox . |

FOREIGN PATENT DOCUMENTS

| | | |
|---|---|---|
| 2573301 | 11/1984 | France . |
| 1099658 | 4/1959 | Germany . |
| 2455174 | 5/1975 | Germany . |
| 2540968 | 3/1977 | Germany . |
| 2823291 | 11/1979 | Germany . |
| 2946728 | 5/1981 | Germany . |
| 3120102 | 12/1982 | Germany . |
| 3510586 | 10/1986 | Germany . |

Primary Examiner—David M. Shay
Attorney, Agent, or Firm—Peter C. Richardson; Lawrence C. Akers; Aaron Passman

[57] ABSTRACT

A control responds to impedance and temperature between active and return electrodes of the electrosurgical generator during tissue desiccation. Tissue contacts separately and independently provide high frequency power to effect tissue electrosurgically. An instantaneous impedance monitor between each contact and the return electrode signals. A regulator receives the signals and separately and independently controls tissue impedance at each contact in accord with signals to change independently the power to the return electrode. A temperature sensor for each contact transmits its temperature to the generator to regulate power to each contact. A first multiplexer provides high frequency electrosurgical power separately and independently to each contact from the generator. A second multiplexer relays temperature amounts of each contact to the generator. A method of control responds to tissue impedance by supplying high frequency power separately and independently to contacts, monitoring, regulating and controlling impedance between the contacts and the return electrode to set the generator power applied by each contact. Transmitting temperature amounts for each contact with sensors regulates contact power.

16 Claims, 3 Drawing Sheets

IMPEDANCE AND TEMPERATURE GENERATOR CONTROL

FIELD OF THE INVENTION

Automatic control for an electrosurgical generator responds to the level of tissue impedance between active and return electrodes. A plurality of active electrode contacts, each capable of separately and independently transmitting high frequency power into the tissue from the active lead of the electrosurgical generator. A plurality of temperature sensors each associated with one of the plurality of active electrode contacts transmit a signal to the indicative of the temperature at the active electrode contact.

BACKGROUND OF THE DISCLOSURE

As a result of manual operation problems, several attempts to provide automatic generator operation when surgical forceps contact patient tissue have been patented. U.S. Pat. No. 2,827,056, German patent 1,099,658, German patent 28 23 291 describe circuits which place a direct current potential across the surgical forceps. Placement of the forceps across patient tissue causes a small DC current to flow therethrough. Direct current flow causes activation of a relay circuit enabling the higher power radio frequency power to flow into the patient's tissue for surgical effect. Selecting fixed resistance values, within the circuits, determine the tissue impedance level below which radio frequency power activation occurs.

Patent German Patent DE 25 40 968 describes a circuit which uses a low-frequency measurement current to determine relative patient tissue impedance; low frequency current flow within a specified amplitude range turns on generator high frequency power for surgical effect. That circuit also includes a time delay relay for controlling time between application of forceps to patient tissue and subsequent generator operation.

Subsequent patents addressed the need for automatic turn off capability during bipolar desiccation procedures. German patent DE 31 20 102 A1 describes a circuit which monitors the differential quotient (time derivative) of patient tissue impedance to determine when to turn off radio frequency power delivery; a point of zero time derivative is selected to turn off power delivery. German patent DE 29 46 728 A1 describes a circuit which turns radio frequency power off after an adjustable, but fixed time delay. German patent DE 35 10586 describes a circuit which uses a low-frequency control current or low level generator radio frequency current source and a current level monitor to turn on generator radio frequency power for surgical effect. The circuit also monitors the generator output voltage for third harmonic content generated when desiccation completes and sparking begins to cause harmonic frequency generation to turn off generator radio frequency power. It is a device which measures current flowing through the tissue and forms a digitized signal of current level. The signal and the manual activation are combined to operate the device.

U.S. Pat. No. 4,860,745 discusses the problems encountered when turning off radio frequency power based upon measurements of the time derivative of patient tissue impedance and, instead, presents a circuit which turns off generator radio frequency power based upon fixed fractional changes ,in the amount of radio frequency current delivered to the patient tissue during desiccation or based upon generator sparking and harmonic frequency generation. A peak detector circuit examines the peak current at the forceps and a second circuit which monitors the decreasing current during coagulation. Measured current levels are converted to voltages within the circuits. The voltages, thus measured, control the electrosurgical generator which is turned off when a fraction of the peak current is greater than the current measured which flows through the tissue during coagulation. If the current flowing through the tissue is greater than the fraction, then the output of the electrosurgical generator is continued until it is less.

German patent 2,455,174 is directed to a switch and relay so when the doctor operates the switch, which is normally closed; it enables ESU control. Opening the switch activates a relay which operates the electrosurgical generator when the impedance value between the forceps is within a predetermined range. These claims are avoided since we have no switch and relay. Also required is a manually activated switch to operate the relay. The switch is on the handle of the forceps.

U.S. Pat. No. 4,658,819 discloses a circuit wherein the power delivered to the electrode is a function of the voltage from a DC supply and the load as measured by sensors of load voltage and current. A microprocessor controller digitizes the sensing signals and computes the load impedance and actual power being delivered. The microprocessor controller accordingly repeats the measurement, calculation and correction process approximately as long as the generator is operating. U.S. Pat. No. 4,372,315 discloses a circuit which measures impedances after delivering a set number of radio frequency pulses on a pulse burst by pulse; burst basis. U.S. Pat. No. 4,321,926 has a feedback system to control dosage but the impedance sensing is not on a real time basis. U.S. Pat. Nos. 3,964,487, 3,980,085, 4,188,927, and 4,092,986 have circuitry to reduce the output current in accordance with increasing load impedance. In those patents voltage output is maintained constant while the current is decreased with increasing load impedance. U.S. Pat. No. 4,094,320 has a circuit that responds to impedance changes as measured by sensing current in the active and return leads. The sensed currents are subtracted from one another and if that exceeds a variable threshold the generator is turned off. The variable threshold is a function of power level and leakage current through stray capacitance.

In French Patent 2,573,301 thermocouple(s) one or two are used as electrodes of a high frequency mono or bipolar tool to monitor temperature of the electrode and prevent sticking of tissue to electrode. U.S. Pat. No. 4,492,231 discusses temperature, blade conductivity and sticking of desiccated blood in a bipolar forceps.

U.S. Pat. Nos. 4,232,676 and 4,314,559 assigned to Corning Glass Works, disclose blades that with areas for electrosurgery and other areas which do not conduct high frequency power. The '676 patent has bipolar electrodes on the same blade so that power passing therebetween will cauterize bleeders. The '559 patent has a first conductive layer for coating the electrosurgical blade and a second Teflon layer to provide a non-stick surface. The conductive layer is such that portions of that layer are exposed and form a connection between surgical blade and the surface such that the Teflon only fills interstices, inclusions and the like at the surface, thus providing the non-stick surface of the cutting or coagulating instrument.

No circuitry has been known to automatically control the power applied by sensitivity to impedance at one or more areas of tissue contact with active electrode contacts on the active tissue electrode and to sense temperature at the active electrode contacts. It is desired to provide consistent desiccation levels of widely varying tissue types even if closely adjacent.

SUMMARY OF THE INVENTION

An automatic control for an electrosurgical generator preferably responds to the level of tissue impedance between active and return electrodes of the electrosurgical generator during tissue desiccation may include the electrosurgical generator with an active lead and a return lead to supply high frequency electrosurgical power. A pair of active electrode tissue contacting members may be positionable against the tissue. The active electrode tissue contacting members connect to the active lead. One or more active electrode contacts might be associated with each active electrode tissue contacting member. Each active electrode contact is preferably capable of separately and independently providing high frequency power supplied from the respective active electrode tissue contacting member in order to electrosurgically effect the tissue.

A return electrode connects to the return lead of the electrosurgical generator and an impedance monitor may be included between each of the active electrode contacts and the return electrode for providing signals of the instantaneous impedances therebetween. A regulator may be connected to receive the signals from the impedance monitor for allowing the electrosurgical generator power to be independently applied by each of the active electrode contacts. The regulator may be operatively associated with the output of the electrosurgical generator to separately and independently control the impedance between each active electrode contacts in accord with monitored impedance signals by the changing of the level of transmission of high frequency power between the electrosurgical generator and the associated active electrode contact for independent regulation of power passing to the return electrode from each active electrode contact.

One or more temperature sensors may be associated with one or more of the active electrode contacts so each temperature sensor may be connected for transmitting a temperature amount to the electrosurgical generator. The temperature amount indicative of at least the temperature at its associated active electrode contact. The regulator is preferably connected to receive the instantaneous temperature amounts and assess changes in the temperature for independently regulating the electrosurgical generator power to each of the active electrode contacts for individually electrosurgically effecting the tissue between each active electrode contact and the return electrode in response to the temperature amount.

An insulated support may carry the pair of the tissue contacting members including one or more of the active electrode contacts. The return electrode may be held in position on the insulated support to capture tissue between the return electrode and one or more of the active electrode tissue contacting members preferably having one or more active electrode contacts for thereby forming a monopolar circuit with the return electrode. At least two of the active electrode tissue contacting members are preferably a forceps carrying one or more active electrode contacts. The contacting members, the active electrode contacts or the return electrode may be in position for movement to and from each other to capture tissue therebetween.

Active electrode tissue contacting members with the return electrode may form the bipolar instrument and might preferably be hinged as a scissors. Shearing edges on the scissors with one or more active electrode contacts and the return electrode electrically isolated from but movably associated therewith for providing an electrosurgical effect therebetween. A first multiplexer is preferably connected to one or more of the active electrode contacts for providing high frequency electrosurgical power to separately and independently supply each active electrode contact from the active lead of the electrosurgical generator. A second multiplexer is preferably connected to one or more of the temperature sensors for providing the temperature amounts to the electrosurgical generator indicative of the temperature about its associated active electrode contact.

An elongate insulated support may carry at least one active electrode contact in position for thereby forming a monopolar electrosurgical electrode for use in a laparoscopic procedure. The insulated support is preferably circular in cross section to cooperatively function as a laparoscopic instrument within a passage through the tissue established by a trocar. A user control is preferably on the electrosurgical generator for setting the level of power desired for electrosurgery.

A method automatically controls the electrosurgical generator preferably in response to the level of tissue impedance between active and return electrodes of the electrosurgical generator. The active electrode may have one or more active electrode contacts used with the steps of supplying electrosurgical power from the electrosurgical generator to active and return electrodes. Positioning against the tissue one or more active electrode contacts associated with the active electrode is a step. Supplying high frequency power separately and independently to each active electrode contact in order to produce an electrosurgically effect on the tissue is another preferred step. Then monitoring separately impedance between one or more of the active electrode contacts and the return electrode for providing signals of the instantaneous impedances therebetween may be an added step. Receiving signals of instantaneous impedance with a regulator for setting electrosurgical generator power to be applied by each of the active electrode contacts is a further step. Controlling separately and independently the electrosurgical generator as a function of the impedance between each of the active electrode contacts and the return electrode is a step that may be accomplished with a regulator for the operational output of the electrosurgical generator. Changing of the level of transmission of high frequency power between the electrosurgical generator and the associated active electrode contact for independent regulation of power passing between the return electrode and each active electrode contact is a step in the method. Providing separate and independent high frequency electrosurgical power with a first multiplexer connection to one or more of the active electrode contacts may be a step of the method.

The method may have the added step of positioning against the tissue one or more one or more temperature sensors each associated with one or more of the active electrode contacts for transmitting from each temperature sensor a temperature amount to the electrosurgical generator indicative of at least the temperature at its associated active electrode contact. Then the method may include the added step of measuring the instantaneous temperature signals to assess changes in the temperature for independently regulating the electrosurgical generator power to each of the active electrode contacts for individually electrosurgically effecting the tissue between each active electrode contact and the return electrode in response to the temperature amount. The added steps of assessing separately and independently the high frequency electrosurgical power with a second multiplexer connection to one or more temperature sensors and providing the signals to the electrosurgical generator indicative of the temperature at its associated active electrode contact may be performed.

DETAILED DESCRIPTION OF THE INVENTION

Figure 1:
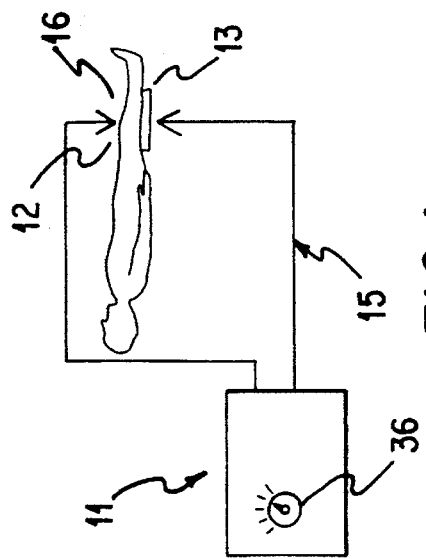
FIG. 1 is a schematic illustration of a monopolar electrosurgical generator circuit including the patient.
Figure 3:
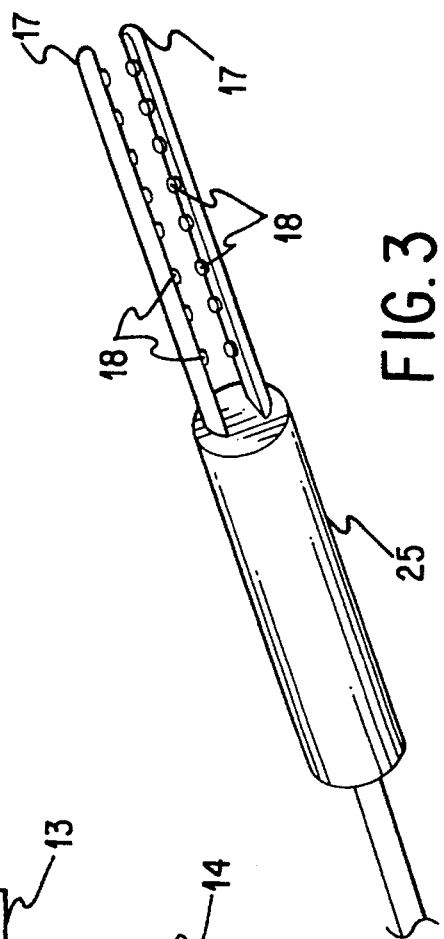
FIG. 3 is a perspective view of a forceps possibly useful as a laparoscopic instrument with a pair of active electrodes with the active electrode contacts and/or the temperature sensors juxtaposed for use in a monopolar circuit with a remotely positioned return electrode in circuit as per FIG. 1; the return electrode is not shown in FIG. 3.
Figure 2:
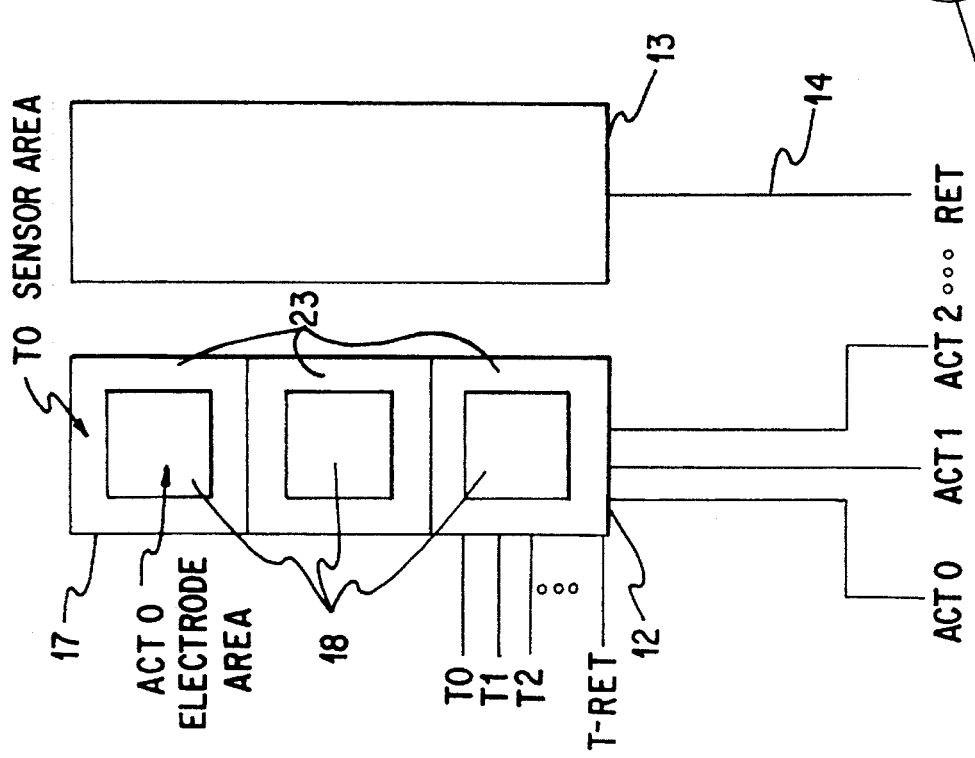
FIG. 2 is an enlarged schematic representation of the active electrode contacts and/or temperature sensors as could be used in the circuit of FIG. 1.
Figure 6:
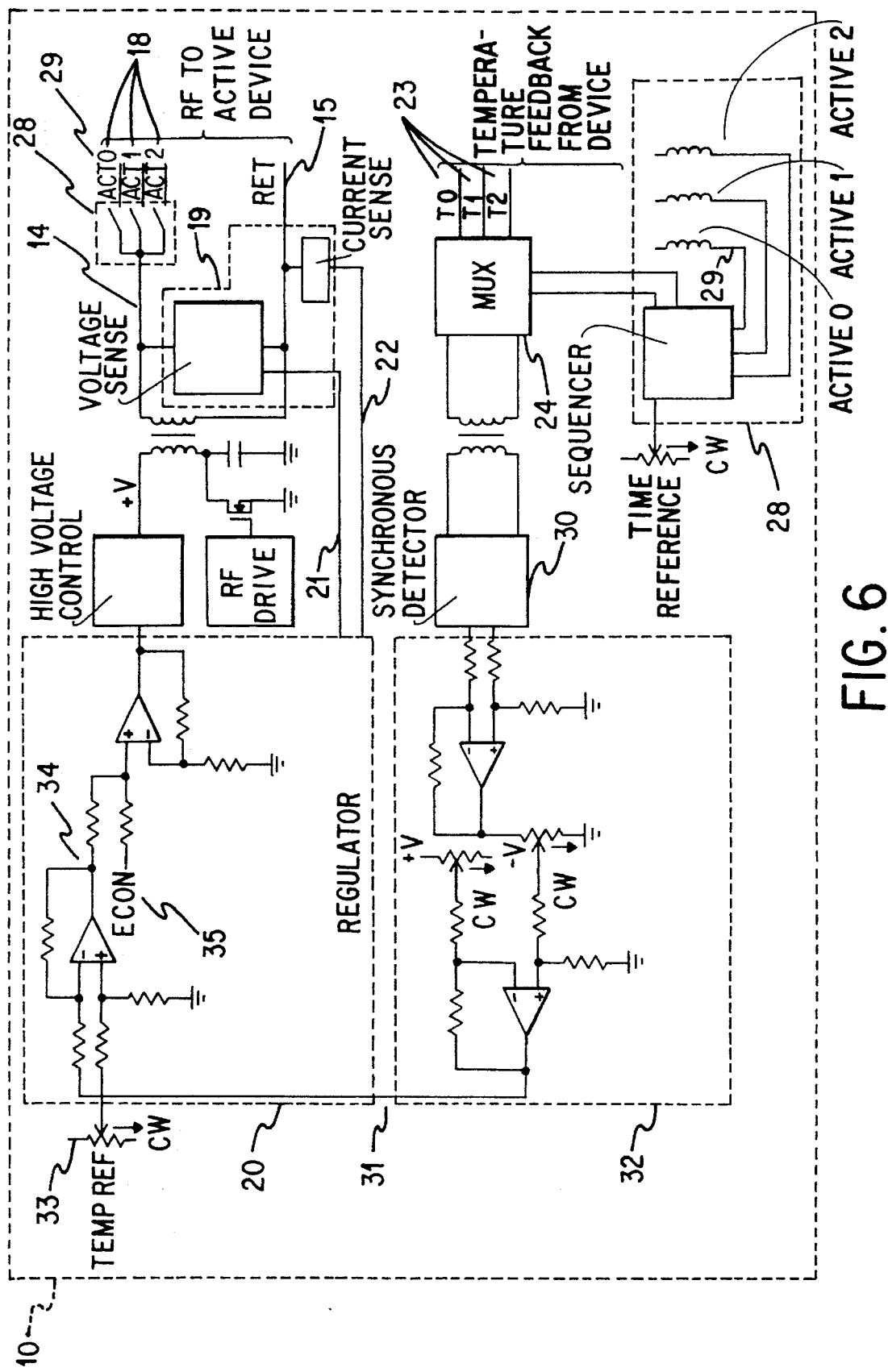
FIG. 6 is a schematic circuit diagram of the impedance monitor and the temperature sensors which are part of the control for the electrosurgical effect.

An automatic control 10 for an electrosurgical generator 11 as shown in FIGS. 1 and 6 responds to the level of tissue impedance between active and return electrodes 12 and 13 for delivery of power from the electrosurgical generator 11 during tissue desiccation includes an automatic control circuit 10 with an active lead 14 and a return lead 15 to supply high frequency electrosurgical power. The monitoring and control of temperature at the electrosurgical site 16 is also a part of this disclosure. A pair of active electrode tissue contacting members 17 as in FIG. 3 are positionable against the tissue so as to clamp tissue therebetween during desiccation. The active electrode tissue contacting members 17 connect to the active lead 14. One or more active electrode contacts 18 as shown in the enlarged view of FIG. 2 are associated with each active electrode tissue contacting member 17. Each active electrode contact 18 is capable of separately and independently providing high frequency power supplied from its respective active electrode tissue contacting member 17 in order to electrosurgically effect the tissue in contact therewith.

The return electrode 13, as shown in the various views of FIGS. 1, 2, 4, and 5 connects to the return lead 15 of the electrosurgical generator 11. An impedance monitor 19 is included between each of the active electrode contacts 18 and the return electrode 13 for providing signals of the instantaneous impedances therebetween. Various approaches to monitoring impedance have been disclosed and typically pickup voltage and current signals from the electrosurgical generator leads 14 and 15 or the electrodes 12 and 13 so that the multiple of the signals can be used to determine the load across the electrodes 12 and 13. Tissue impedance monitoring is disclosed in issued patents, such as U.S. Pat. Nos. 4,922,210 and 4,969,885; this disclosure is not to be limited to any particular monitor for impedance and those noted patents are only incorporated herein by reference for purposes of ennoblement and by way of example.

A regulator 20 is connected to receive signals 21 and 22 from the impedance monitor 19 for allowing electrosurgical generator 11 power to be applied to the tissue by each of the active electrode contacts 18. The regulator 20 as will be explained is also involved with the control of the temperature at the active electrode contacts 18. The regulator 20 is operatively associated with the output of the electrosurgical generator 11 to separately and independently control the impedance between each active electrode contacts 18 in accord with monitored impedance signals by the changing of the level of transmission of high frequency power between the electrosurgical generator 11 and the associated active electrode contact 18 for independent regulation of power passing to the return electrode 13 from each active electrode contact 18. This approach recognizes the reality of the variations in tissue impedance in closely located tissues and seeks to accommodate those variations with the automatic control 10 that responds to the tissue at each active electrode contact 18.

One or more temperature sensors 23 are in one embodiment associated with one or more of the active electrode contacts 18 so each temperature sensor 23 is connected for transmitting a temperature amount to the electrosurgical generator 11. The recognition of temperature at the active electrode contact 18 is significant because the desiccation of tissue is preferably accomplished if the temperature of the desiccation process is controlled thus preventing over heating which among other problems results in the sticking of the active electrode contacts 18 and the return electrode 13 to the desiccated tissue. Sticking causes tearing of the coagulated tissue proteins and thus destroys the sought after coagulum. The temperature amount is indicative of at least the temperature at its associated active electrode contact 18. The temperature amount from the temperature sensors 23 near the active electrode contacts 18 is transmitted through a second multiplexer 24.

Figure 4:
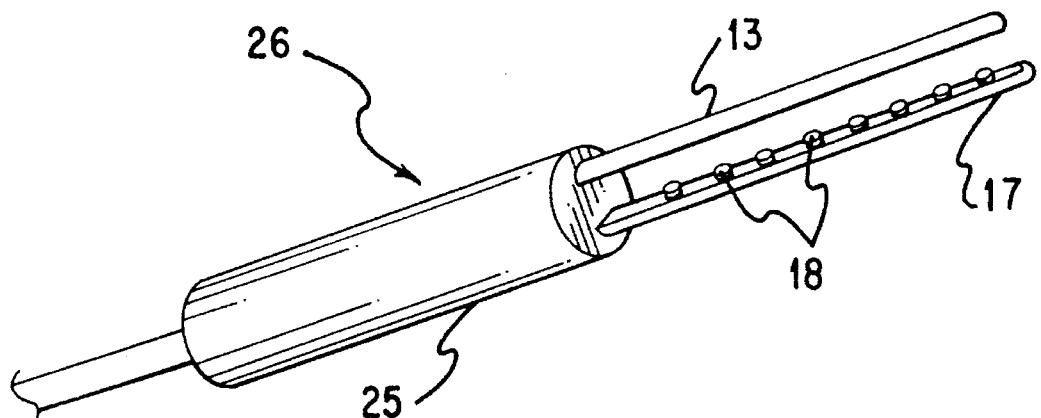
FIG. 4 is a perspective view of a bipolar forceps possibly useful as a laparoscopic instrument with an active electrode having active electrode contacts and/or temperature sensors movably positioned across for selective contact with the return electrode.
Figure 5:
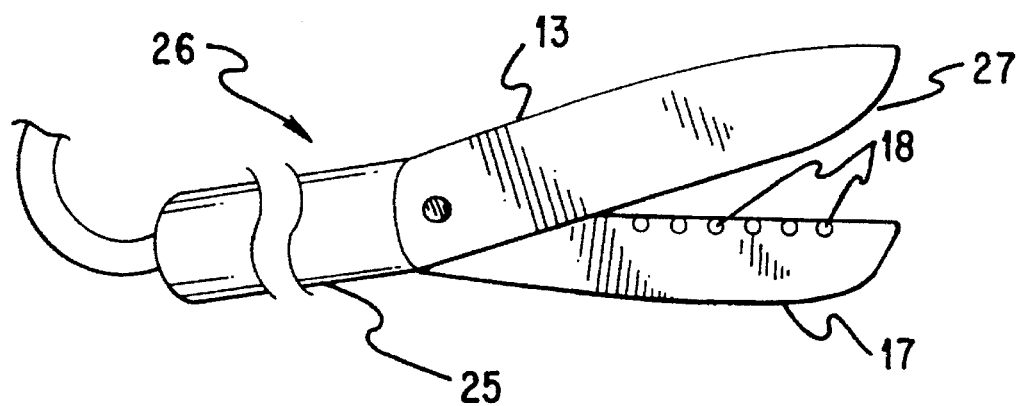
FIG. 5 is a side view of a bipolar scissors with active and return electrodes wherein the active electrode has active electrode contracts and/or temperature sensors.

An insulated support 25 is an alternative shown in FIGS. 3, 4 and 5, carries the pair of the tissue contacting members 17 including one or more of the active electrode contacts 18. The return electrode 13 in FIG. 4 and 5 is held in position on the insulated support 25 juxtaposed for movement to capture tissue between the return electrode 13 and one or more of the active electrode tissue contacting members 17 preferably having one or more active electrode contacts 18 for thereby forming a bipolar instrument 26. FIG. 3 is unique in that it has two opposed active electrode tissue contacting members 17, which clamp tis, sue therebetween, cause the active electrode contacts 18 thereon to desiccate the tissue by a completed circuit with the return electrode 13 remotely located such as depicted in FIG. 1. Thus at least two of the active electrode tissue contacting members 17 may function as the bipolar instrument 26 and are preferably a forceps type which carries the one or more active electrode contacts 18. The tissue contacting members 17, the active electrode contacts 18 or the return electrode 13 each may be in position for movement to and from each other to capture tissue therebetween.

At least two of the active electrode tissue contacting members 17 or one with the return electrode 13, such as in FIG. 4, may form the bipolar instrument 26 or might alternatively be hinged as a scissors, as in FIG. 5. The scissors has shearing edges 27 with one or more active electrode contacts 18 and the return electrode 13 electrically isolated from but accurately and movably associated therewith for providing an electrosurgical and mechanical cutting effect therebetween.

A first multiplexer 28 is preferably connected to one or more of the active electrode contacts 18 for providing high frequency electrosurgical power separately and independently to each active electrode contact 18 from the active lead 14 of the electrosurgical generator 11. In FIG. 6 the first and a second multiplexer 28 and 24 are shown. Specifically, the first multiplexer 28 will activate active 29 (Act 0) and energy is then delivered from the electrosurgical generator to the tissue thereat. A feedback algorithm controls the amount of power delivered to the tissue as a function of the impedance signal and temperature amount at (Act 0) 29. Desiccation is completed by delivering power in accord with a preferred curve for amount of the delivering power in connection with specific impedance signals and temperature amounts. Tissue impedance establishes the end point for power delivery since the change in impedance signal is dramatic when the tissue moisture is gone.

The regulator 20 includes a thermal curve for the derivative of temperature amount with respect to time, the desired temperature at which the tissue is to remain and the time for which the temperature should be maintained. As an alternative to the latter, the regulator 20 responds to a tissue impedance signal to indicate the end point so a derivative of the tissue impedance signal will give the instantaneous end point condition. The final tissue impedance signal of complete desiccation may be related to the initial tissue impedance signal before power delivery, i.e. the nature of the tissue could establish the thermal curve. A synchronous detector 30 in FIG. 6 retrieves the temperature amount in the high frequency field in the tissue produced by the electrosurgical generator 11. The instantaneous temperature amounts are assessed and any changes in the temperature at any active electrode contacts 18 are independently regulated by the electrosurgical generator 11 power delivery to each of the active electrode contacts 18 thus individually electrosurgically effecting the tissue between each active electrode contact 18 and the return electrode 13 in response to the temperature amount. A thermal feedback 31 to monitor temperature sensors 23 and specifically the temperature amount so the exact power delivered from the electrosurgical generator 11 to the tissue is controlled accordingly. A signal conditioning circuit 32 allows the temperature amount to be amplified and scaled so that the result has an identifiable volts per degree relationship.

An output of the signal conditioning circuit 32 is compared against the thermal curve, e.g. in FIG. 6 as a potentiometer 33 setting. A difference 34 between the temperature amount and that established by the curve is combined with the high voltage control 35 for the RF drive of the electrosurgical generator 11 to vary that as a function of temperature. After completion of desiccation on (Act 0) 29 the process is repeated for (Act 1, 2, 3 etc).

The second multiplexer 24 is preferably connected to one or more of the temperature sensors 23 for providing the temperature amounts to the electrosurgical generator 11 indicative of the temperature about its associated active electrode contact 18.

The elongate insulated support 25 in FIGS. 3, 4 and 5 carry at least one active electrode contact 18 in position for thereby forming a monopolar or bipolar electrosurgical device as explained and if the insulated support 25 is sufficiently elongate for use in a laparoscopic procedure then the active electrode contacts 18 can be used accordingly. The insulated support 25 is preferably circular in cross section to cooperatively function as a laparoscopic instrument within a passage through the tissue established by a trocar (not shown). Since laparoscopy is not the main thrust of this disclosure and because the concept of a trocar passage is well known by practitioners specifics are not included. A user control 36 in FIG. 1 is on the electrosurgical generator 11 for setting the level of power desired for electrosurgery many approached are in the field for setting the level of power desired and one that is commercial is the control on the Force 40 electrosurgical generator 11 by Valleylab of Boulder, Colo. A method automatically controls the electrosurgical generator 11 in response to the level of tissue impedance between active and return electrodes 12 and 13 of the electrosurgical generator 11. The active electrode 12 has one or more active electrode contacts 18 used with the steps of supplying electrosurgical power from the electrosurgical generator 11 to active and return electrodes 12 and 13. Positioning against the tissue one or more active electrode contacts 18 associated with the active electrode 12 is a step. Supplying high frequency power separately and independently to each active electrode contact 18 in order to produce an electrosurgically effect in the tissue is another preferred step. Then monitoring separately impedance between one or more of the active electrode contacts 18 and the return electrode 13 for providing signals of the instantaneous impedances therebetween is an added step. Receiving signals of instantaneous impedance with the regulator 20 for setting the electrosurgical generator 11 power to be applied by each of the active electrode contacts 18 is a further step. Controlling separately and independently the electrosurgical generator as a function of the impedance between each of the active electrode contacts 18 and the return electrode 13 is a step accomplished with a regulator 20 for changing the operational output of the electrosurgical generator 11. Changing of the level of transmission of high frequency power between the electrosurgical generator 11 and the associated active electrode contact 18 for independent regulation of power passing between the return electrode 13 and each active electrode contact 18 is another step in the method. Providing separate and independent high frequency electrosurgical power with a first multiplexer 28 connection to one or more of the active electrode contacts 18 is a step of the method.

The method may have the added step of positioning against the tissue one or more one or more temperature sensors 23 each associated with one or more of the active electrode contacts 18 for transmitting from each temperature sensor 23 a temperature amount to the electrosurgical generator 11 indicative of at least the temperature at its associated active electrode contact 18 at the same time the impedance is monitored. Then the method includes the added step of measuring the instantaneous temperature signals to assess changes in the temperature for independently regulating the electrosurgical generator 11 power to each of the active electrode contacts 18 for individually electrosurgically effecting the tissue between each active electrode contact 18 and the return electrode 13 in response to the temperature amount. The added step of assessing separately and independently the high frequency electrosurgical power with a second multiplexer 24 connection to one or more temperature sensors 23 and providing the signals to the electrosurgical generator 11 indicative of the temperature at its associated active electrode contact 18 may be performed.

What is claimed is:

1. An automatic control for electrosurgical generator power responsive separately and independently to the level of tissue impedance between active and return electrodes of the electrosurgical generator during tissue desiccation comprising:

an electrosurgical generator having an active electrode and a return electrode in circuit with the tissue and connected to the electrosurgical generator with an active lead and a return lead respectively so as to supply high frequency electrosurgical power to the tissue therebetween the active electrode and return electrode;

a plurality of active electrode contacts electrically coupled to and associated with the active electrode, each active electrode contact on the active electrode and positioned for contact with tissue so as to be capable of separately and independently providing high frequency power supplied by the electrosurgical generator through the active lead to the active electrode and the active contacts thereon to electrosurgically effect the tissue thereagainst;

a monitor connected in circuit between each of the active electrode contacts and the return electrode, the monitor responsive separately and independently to voltage across and current flow through each of the active electrode contacts, the tissue and the return electrode for application in providing impedance signals of instantaneous impedances therebetween, and a regulator electrically linked in circuit and associated with an operational output of the electrosurgical generator for separately and independently controlling the electrosurgical generator as a function of tissue impedance between each active electrode contact and the return electrode in accord with monitored impedance signals, the regulator connected in circuit with the electrosurgical generator for changing a level of transmission of high frequency power between the electrosurgical generator and the associated active electrode contact for independent regulation of power passing to the return electrode from each active electrode contact.

2. The automatic control for an electrosurgical generator responsive separately and independently to the level of tissue impedance between each of the active contacts and the return electrode of claim 1 wherein one or more temperature sensors each associated with one or more of the active electrode contacts, each temperature sensor connected for transmitting a temperature amount to the electrosurgical generator indicative of at least the temperature at an associated active electrode contact, and the monitor connected to receive instantaneously temperature amounts and assess changes in the temperature amounts for separately and independently regulating the electrosurgical generator power to each of the active electrode contacts for individually electrosurgically effecting the tissue between each active electrode contact and the return electrode in accord with a temperature amount.

3. The automatic control for an electrosurgical generator responsive separately and independently to the level of tissue impedance between each of the active electrode contacts and the return electrode of claim 2 wherein a first multiplexer is electrically connected to one or more of the active electrode contacts, the first multiplexer for providing high frequency electrosurgical power separately and independently to each active electrode contact from the electrosurgical generator.

4. The automatic control for an electrosurgical generator responsive separately and independently to the level of tissue impedance between each of the active electrode contacts and the return electrode of claim 2 wherein a second multiplexer is electrically connected to one or more of the temperature sensors, the second multiplexer for providing signals of the temperature amounts sensed to the electrosurgical generator indicative of the temperature about an associated active electrode contact.

5. The automatic control for an electrosurgical generator responsive separately and independently to the level of tissue impedance between each of the active electrode contacts and the return electrode of claim 2 wherein a first multiplexer is electrically connected to one or more of the active electrode contacts, the first multiplexer for providing high frequency electrosurgical power separately and independently to each active electrode contact from the electrosurgical generator, and wherein a second multiplexer is electrically connected to one or more temperature sensors, the second multiplexer for providing signals of the temperature amounts sensed to the electrosurgical generator indicative of the temperature at an associated active electrode contact.

6. The automatic control for an electrosurgical generator responsive separately and independently to the level of tissue impedance between each of the active electrode contacts and the return electrode of claim 2 wherein a user control is located on the electrosurgical generator, the user control is electrically connected for setting the level of power desired for electrosurgery.

7. The automatic control for an electrosurgical generator responsive separately and independently to the level of tissue impedance between each of the active electrode contacts and the return electrode of claim 2 wherein an elongate insulated support carries at least one of the active electrode contacts in a position for thereby forming a monopolar electrosurgical electrode for use in a laparoscopic procedure.

8. The automatic control for an electrosurgical generator responsive separately and independently to the level of tissue impedance between each of the active electrode contacts and the return electrode of claim 7 wherein the insulated support is circular in cross section to cooperatively function as a laparoscopic instrument within a passage through the tissue established by a trocar.

9. The automatic control for an electrosurgical generator responsive separately and independently to the level of tissue impedance between each of the active electrode contacts and the return electrode of claim 2 wherein an insulated support carries a pair of members including one or more of the active electrode contacts on one of the pair of members, and the return electrode on another of the members, the pair held in position on the insulated support to capture tissue between the return electrode and one or more of the active electrode tissue contacting members for thereby forming a bipolar instrument.

10. The automatic control for an electrosurgical generator responsive separately and independently to the level of tissue impedance between each of the active electrode contacts and the return electrode of claim 9 wherein the pair of members forming the bipolar instrument include a forceps which carries the one or more active electrode contacts and the return electrode in position for movement to and from each other to capture tissue therebetween.

11. The automatic control for an electrosurgical generator responsive separately and independently to the level of tissue impedance between each of the active electrode contacts and the return electrode of claim 9 wherein the members forming the bipolar instrument and are hingedly joined as a scissors with the members thereof having shearing edges with one or more active electrode contacts and the return electrode electrically isolated for providing an electrosurgical effect therebetween.

12. An automatic control for an electrosurgical generator responsive separately and independently to the level of tissue impedance between active and the return electrode of the electrosurgical generator during tissue desiccation comprising:

an electrosurgical generator having an active lead and a return lead connected thereto to supply high frequency electrosurgical power;

a pair of active electrode tissue contacting members positionable against the tissue, the active electrode tissue contacting members connected to the active lead;

a plurality of active electrode contacts associated with each of the pair active electrode tissue contacting members, each active electrode contact in circuit with the tissue and capable of separately and independently providing high frequency power supplied to the respective active electrode tissue contacting member in order to electrosurgically effect the tissue in contact with each active electrode contact;

a return electrode connected to the return lead of the electrosurgical generator, the return electrode in circuit with the tissue, and a monitor connected in circuit between each of the active electrode contacts and the return electrode, the monitor separately and independently responsive to voltage across and current flow though the active electrode contacts, the tissue and the return electrode for application in providing signals instantaneously of impedances therebetween;

one or more temperature sensors each associated with one or more of the active electrode contacts and each temperature sensor connected for transmitting a temperature amount to the electrosurgical generator indicative of at least the temperature amount at an associated active electrode contact and the monitor connected to receive instantaneously the temperature amounts and assess temperature changes for use in separately and independently regulating the electrosurgical generator power to each of the active electrode contacts to individually electrosurgically effect the tissue between each active electrode contact and the return electrode in response to the sensed temperature amount;

a regulator electrically linked in circuit with and associated with the power output of the electrosurgical generator for separately and independently controlling the electrosurgical generator as a function of the signalled impedance between each active electrode contact in accord with the impedance monitored and the temperature amount sensed, the regulator connected in circuit with the electrosurgical generator for changing a level of transmission of high frequency power between the electrosurgical generator and the associated active electrode contact for independent regulation of power passing between the return electrode and each active electrode contact;

a first multiplexer electrically coupled to the active electrode contacts, the first multiplexer for providing high frequency electrosurgical power separately and independently to each active electrode contact from the active lead of the electrosurgical generator, and a second multiplexer electrically coupled to one or more temperature sensors, the second multiplexer for providing the temperature amounts to the electrosurgical generator indicative of the temperature at its associated active electrode contact.

13. A method for automatically controlling an electrosurgical generator responsive separately and independently to the level of tissue impedance between active and return electrodes of the electrosurgical generator, the active electrode having a plurality of active electrode contacts having the steps of:

supplying electrosurgical power from an electrosurgical generator to the active and return electrodes;

positioning against the tissue one or more of the active electrode contacts associated with the active electrode;

supplying high frequency power separately and independently to each active electrode contact in order to produce an electrosurgically effect on the tissue thereagainst;

monitoring separately and independently impedance between one or more of the active electrode contacts and the return electrode for providing signals of the instantaneous impedances therebetween;

receiving signals of instantaneous impedance with a regulator for setting electrosurgical generator power to be applied by each of the active electrode contacts;

controlling separately and independently the electrosurgical generator as a function of the impedance between each of the active electrode contacts and the return electrode with the regulator for changing the level of transmission of high frequency power between the electrosurgical generator and the associated active electrode contact for independent regulation of power passing between the return electrode and each active electrode contact, and providing separate and independent high frequency electrosurgical power with a first multiplexer electrically coupled to one or more of the active electrode contacts.

14. The method of claim 13 with the added steps of positioning against the tissue one or more one or more temperature sensors each associated with one or more of the active electrode contacts and transmitting from each temperature sensor a temperature amount to the electrosurgical generator, the temperature amount indicative of at least the temperature at associated active electrode contact.

15. The method of claim 14 with the added step of monitoring the instantaneous temperature amounts to assess changes in the temperature for separately and independently regulating the electrosurgical generator power to each of the active electrode contacts for individually electrosurgically affecting the tissue between each active electrode contact and the return electrode in response to temperature.

16. The method of claim 15 with the added step of providing separate and independent high frequency electrosurgical power with a second multiplexer connection to the temperature sensors and providing the temperature amounts to the electrosurgical generator indicative of the temperature at each associated active electrode contact.

* * * * *